United States Patent [19]

Andrae

[11] Patent Number: 4,891,468
[45] Date of Patent: Jan. 2, 1990

[54] DEVICE TO SHIELD AGAINST AN ELECTROMAGNETIC FIELD

[76] Inventor: Franz Andrae, Marionigasse 2-6, Vienna, Austria

[21] Appl. No.: 262,622

[22] Filed: Oct. 26, 1988

[51] Int. Cl.⁴ .............................................. H05K 9/00
[52] U.S. Cl. ................................... 174/35 M S; 342/4
[58] Field of Search ................. 174/35 M S; 361/424; 342/1, 4

[56] References Cited

U.S. PATENT DOCUMENTS 3,177,334  4/1965  Kinkle ..................... 174/35 M S X
3,745,466  7/1973  Pisano ..................... 174/35 M S X

FOREIGN PATENT DOCUMENTS 3015105  10/1981  Fed. Rep. of Germany .
3034964  3/1982   Fed. Rep. of Germany .
3232224  11/1983  Fed. Rep. of Germany .
3327166  4/1984   Fed. Rep. of Germany .
3515541  12/1985  Fed. Rep. of Germany .
1593525  7/1981   United Kingdom .

Primary Examiner—Leo P. Picard
Assistant Examiner—David A. Tone
Attorney, Agent, or Firm—Marmorek, Guttman & Rubenstein

[57] ABSTRACT

Figure 1:
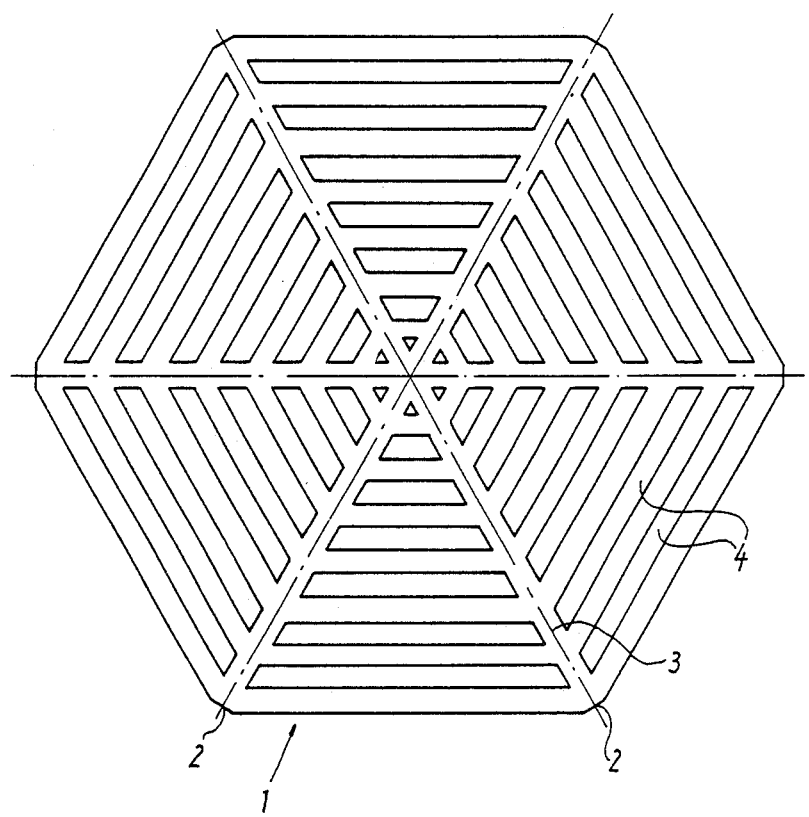

Device to shield against an electromagnetic field, consisting of a shielding film made of metal, in particular aluminum or metallized plastic which is provided with openings, the shielding film having an essentially hexagonal outline and being subdivided into six triangular fields by ridges connecting the corners to the center of the film and the openings consisting of slits which are parallel to the hexagon side of each triangular field and to each other and extend over the entire triangular field (FIG. 1).

6 Claims, 2 Drawing Sheets

DEVICE TO SHIELD AGAINST AN ELECTROMAGNETIC FIELD

The instant invention relates to a device consisting of a shielding film of metal, in particular aluminum, or metallized plastic having openings, to shield against an electromagnetic field.

A device of this type known from DE-OS 32 32 224 is rectangular, whereby the film is provided on its entire surface or on portions of that surface regularly or irregularly distributed recesses and is laminated on a support material. The manufacture of such a film and its application are however relatively expensive. In addition, the rectangular shape produces only a limited shielding effect in practice.

The instant invention intends to create an easy-to-handle device of the type indicated initially which can be adapted to existing requirements and inventively achieves this objective in that the shielding film is essentially hexagonal, is subdivided into six triangular fields by ridges connecting the corners to the center of the film and in that the openings consist of slits which are parallel to the hexagon side of each triangular field and to each other and extend over the entire triangular field.

The device according to the invention has the advantage that it can be used as an insert in a resistive body, preferably a wooden body which is easy to handle and the form of which makes it possible to line up several bodies next to each other if necessary. This device has surprisingly proven to be extremely effective against the damaging effects of electromagnetic fields, whereby it obviously offers nearly parallel circuit segments for all field directions because of its symmetric form. The device can be installed easily in such locations as near a bed or a seat, etc.

According to a preferred embodiment of the invention, the shielding film is placed between two essential hexagonal plates made of plywood or similar material which are glued to each other. In this case one of the plates can be provided with a circular recess to hold the shielding film.

Figures 2, 3:
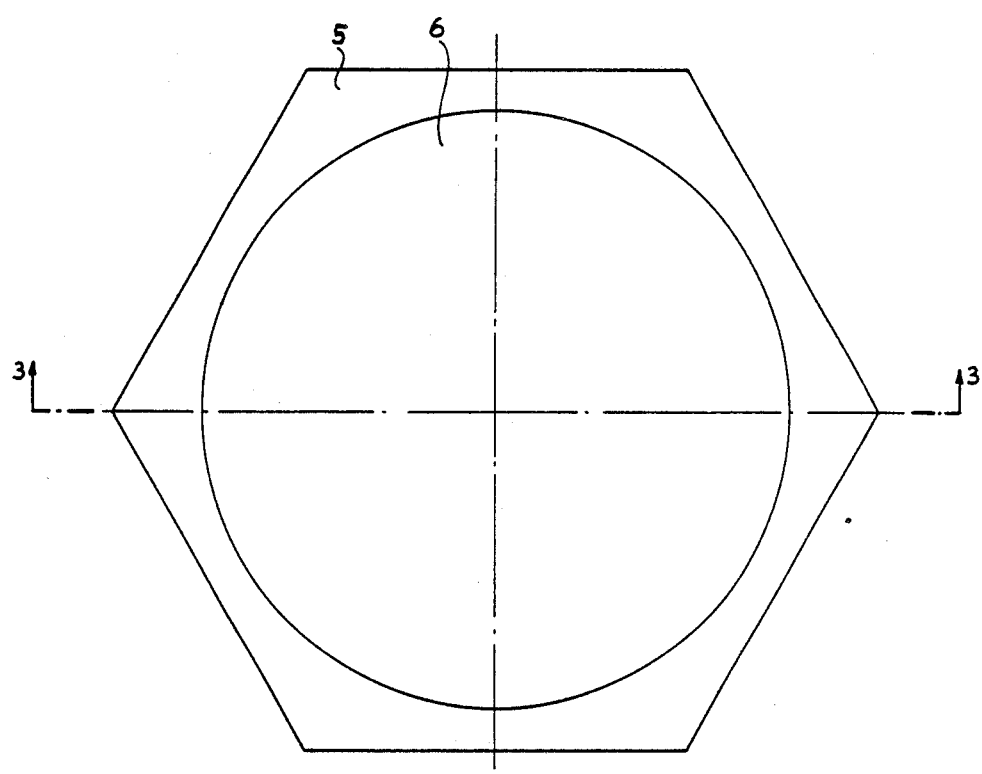

The invention is described in greater detail below through an embodiment and with reference to drawings in which FIG. 1 shows a top view of a device according to the invention, and FIGS. 2 and 3 show a top view and a section along line 3—3 of a plate serving to hold the device according to the invention.

According to FIG. 1 the shielding film 1 which is made of aluminum has an essentially hexagonal outline and is subdivided into six triangular fields by ridges 3 connecting the corners 2 to the center of the film. The openings 4 consist of slits which are parallel to the hexagon side of each triangular field and to each other and extend over the entire triangular field.

The shielding film 1 is placed between two essentially hexagonal plates 5 made of plywood or similar material which are glued to each other. In one of the plates which is shown in FIGS. 2 and 3, a circular recess 6 is made to hold the shielding film. However, the wooden body which holds the shielding film could also have a different outline than that of the shielding film.

I claim:

1. Device to shield against an electromagnetic field, comprising a shielding film made of metal, said shielding film being provided with openings, said shielding film having an essentially hexagonal outline with sides, corners, and a center, said shielding film being subdivided into six triangular fields by ridges connecting the corners to the center of said shielding film, said openings comprising slits which are parallel to the hexagonal side of each triangular field and to each other, said slits extending over the entire triangular field.

2. The device of claim 1 wherein said shielding film is made of aluminum.

3. The device of claim 1 wherein said shielding film is made of metalized plastic.

4. The device of claim 1 further comprising two essentially hexagonal plates which are adhered to each other, said shielding film being disposed between said hexagonal plates.

5. The device of claim 4 wherein said hexagonal plates are made of plywood.

6. The device of claim 4 wherein one of said plates includes a circular recess for receiving said shielding film.

* * * * *